(12) United States Patent
Branch

(10) Patent No.: US 9,103,734 B2
(45) Date of Patent: Aug. 11, 2015

(54) IMPACT INDICATOR

(75) Inventor: Clinton A. Branch, Jacksboro, TX (US)

(73) Assignee: ShockWatch, Inc., Dallas, TX (US)

(*) Notice: Subject to any disclaimer, the term of this patent is extended or adjusted under 35 U.S.C. 154(b) by 741 days.

(21) Appl. No.: 13/415,936

(22) Filed: Mar. 9, 2012

(65) Prior Publication Data

US 2012/0227463 A1 Sep. 13, 2012

Related U.S. Application Data

(60) Provisional application No. 61/451,143, filed on Mar. 10, 2011.

(51) Int. Cl.
| | |
|---|---|
| *G01L 5/00* | (2006.01) |
| *G01P 15/03* | (2006.01) |
| *H01H 35/14* | (2006.01) |
| *H01H 9/16* | (2006.01) |

(52) U.S. Cl.
CPC ............ *G01L 5/0052* (2013.01); *G01P 15/036* (2013.01); *H01H 35/14* (2013.01); *H01H 9/16* (2013.01)

(58) Field of Classification Search
CPC ......... G01P 15/04; G01P 15/02; G01P 15/03; G01P 15/00; G01P 15/036; G01L 5/00; G01L 23/00; G01L 5/0052; G01N 3/30; G01N 35/14; G01N 9/16
USPC ................ 116/203, 200–201, 211–212, 215; 73/12.01, 12.04, 12.05, 12.06, 12.09, 73/12.13
See application file for complete search history.

(56) References Cited

U.S. PATENT DOCUMENTS

| | | |
|---|---|---|
| 2,825,297 A | 3/1958 | Harrison |
| 2,976,732 A | 3/1961 | Hautly |
| 3,021,813 A | 2/1962 | Rips |
| 3,312,188 A | 4/1967 | Lode et al. |
| 3,373,716 A | 3/1968 | Williams |
| 3,461,730 A | 8/1969 | Peters |
| 3,623,449 A | 11/1971 | Knutson |
| 3,707,722 A | 12/1972 | Itoh |
| 3,782,204 A | 1/1974 | Boardman |

(Continued)

FOREIGN PATENT DOCUMENTS

JP 2009156726 7/2009

OTHER PUBLICATIONS

International Search Report and Written Opinion; International Application No. PCT/US2012/028423; 9 pages.

*Primary Examiner* — R. A. Smith
*Assistant Examiner* — Tania Courson
(74) *Attorney, Agent, or Firm* — James L. Baudino

(57) ABSTRACT

According to one aspect of the present disclosure, a device and technique for impact detection is disclosed. The impact indicator includes a housing and a mass member located within the housing. The housing is configured to enable movement of the mass member from a first position to a second position within the housing in response to receipt of an acceleration event by the housing. The impact indicator also includes a spring member disposed within the housing and configured to bias the mass member to the first position, and wherein in response to receipt by the housing of the acceleration event, the mass member is configured to overcome the bias and move from the first position to the second position. The mass member is configured to rotate within the housing in the second position to enable retention of the mass member in the second position.

19 Claims, 3 Drawing Sheets

(56) References Cited

U.S. PATENT DOCUMENTS

| | | |
|---|---|---|
| 3,909,568 A | 9/1975 | Greenhut |
| 4,068,613 A | 1/1978 | Rubey |
| 4,125,085 A | 11/1978 | Rubey |
| 4,177,751 A | 12/1979 | Rubey |
| 4,237,736 A | 12/1980 | Wright |
| 4,361,106 A | 11/1982 | Eklof |
| 4,688,244 A | 8/1987 | Hannon et al. |
| 4,982,684 A | 1/1991 | Rubey |
| 5,027,105 A | 6/1991 | Dailey et al. |
| 5,051,725 A | 9/1991 | Caccitolo |
| 5,153,561 A | 10/1992 | Johnson |
| 5,269,252 A * | 12/1993 | Nagai ........................... 116/203 |
| 5,347,274 A | 9/1994 | Hassett |
| 6,272,901 B1 | 8/2001 | Takeuchi et al. |
| 6,685,094 B2 | 2/2004 | Cameron |
| 6,848,389 B1 | 2/2005 | Elsasser et al. |
| 7,119,759 B2 | 10/2006 | Zehner et al. |
| 7,219,619 B2 | 5/2007 | Fitzer et al. |
| 7,353,615 B1 | 4/2008 | Branch |
| 7,509,835 B2 | 3/2009 | Beck |
| 8,671,582 B2 * | 3/2014 | Branch ........................... 33/365 |
| 2005/0039669 A1 | 2/2005 | Elsasser et al. |
| 2007/0194943 A1 | 8/2007 | Fitzer et al. |
| 2009/0249858 A1 | 10/2009 | Ishikawa et al. |
| 2009/0307827 A1 | 12/2009 | Aspray |
| 2012/0227661 A1 * | 9/2012 | Branch et al. ................. 116/203 |
| 2013/0247814 A1 * | 9/2013 | Branch ........................... 116/203 |

\* cited by examiner

IMPACT INDICATOR

BACKGROUND

During manufacturing, storage or transit, many types of objects need to be monitored due to the sensitivity or fragility of the objects. For example, some types of objects may be susceptible to damage if dropped or a significant impact is received. Thus, for quality control purposes and/or the general monitoring of transportation conditions, it is desirable to determine and/or verify the environmental conditions to which the object has been exposed.

BRIEF SUMMARY

According to one aspect of the present disclosure, a device and technique for impact detection and indication is disclosed. The impact indicator includes a housing and a mass member located within the housing. The housing is configured to enable movement of the mass member from a first position to a second position within the housing in response to receipt of an acceleration event by the housing. The impact indicator also includes a spring member disposed within the housing and configured to bias the mass member to the first position, and wherein in response to receipt by the housing of the acceleration event, the mass member is configured to overcome the bias and move from the first position to the second position. The mass member is configured to rotate within the housing in the second position to enable retention of the mass member in the second position.

According to another embodiment of the present disclosure, an impact indicator includes a housing and a mass member located within the housing. The housing is configured to enable movement of the mass member from a first position to a second position within the housing in response to receipt by the housing of a first acceleration event. The impact indicator also includes a spring member disposed within the housing and configured to bias the mass member to the first position, and wherein in response to receipt by the housing of the first acceleration event, the mass member overcomes the bias and moves from the first position to the second position. The impact indicator further includes a first latch element located proximate to a first side of the mass member and a second latch element located proximate to a second side of the mass member opposite the first side and offset from the first latch element. At least one of the first and second latch elements is configured to engage a corresponding latch element located on the mass member to retain the mass member in the second position in response to the housing receiving a second acceleration event in a direction opposite the first acceleration event.

According to another embodiment of the present disclosure, an impact indicator includes a housing and a mass member located within the housing. The housing has a plurality of sidewalls forming a translation path to enable movement of the mass member from a first position to a second position within the housing in response to receipt by the housing of an acceleration event. The impact indicator also includes a spring member disposed within the housing and configured to bias the mass member to the first position, and wherein in response to receipt by the housing of the acceleration event, the mass member moves from the first position to the second position and the spring member bears on the mass member to cause rotation of the mass member in the second position to facilitate retention of the mass member in the second position.

BRIEF DESCRIPTION OF THE SEVERAL VIEWS OF THE DRAWINGS

For a more complete understanding of the present application, the objects and advantages thereof, reference is now made to the following descriptions taken in conjunction with the accompanying drawings, in which.

DETAILED DESCRIPTION

Embodiments of the present disclosure provide a device and technique for impact detection and indication. According to one embodiment, an impact indicator includes a housing and a mass member located within the housing. The housing is configured to enable movement of the mass member from a first position to a second position within the housing in response to receipt of an acceleration event by the housing. The impact indicator also includes a spring member disposed within the housing and configured to bias the mass member to the first position, and wherein in response to receipt by the housing of the acceleration event, the mass member is configured to overcome the bias and move from the first position to the second position. The mass member is configured to rotate within the housing in the second position to enable retention of the mass member in the second position. Embodiments of the present disclosure enable impact and/or acceleration event detection and indication while preventing or substantially preventing a re-setting of the state of the impact indicator once a predetermined level or magnitude of impact has occurred. For example, in some embodiments, the mass member of the indicator is configured to rotate in response to moving from a non-activated position to an activated position to facilitate retention of the mass member in the activated position once the indicator has been activated. Further, embodiments of the present disclosure further enable retention of the mass member in the activated position once the indicator has been activated by using a plurality of offset latches that are configured to engage the mass member if the indicator receives an acceleration event that may be performed in an attempt to re-set the indicator to the non-activated state.

Figure 1A:
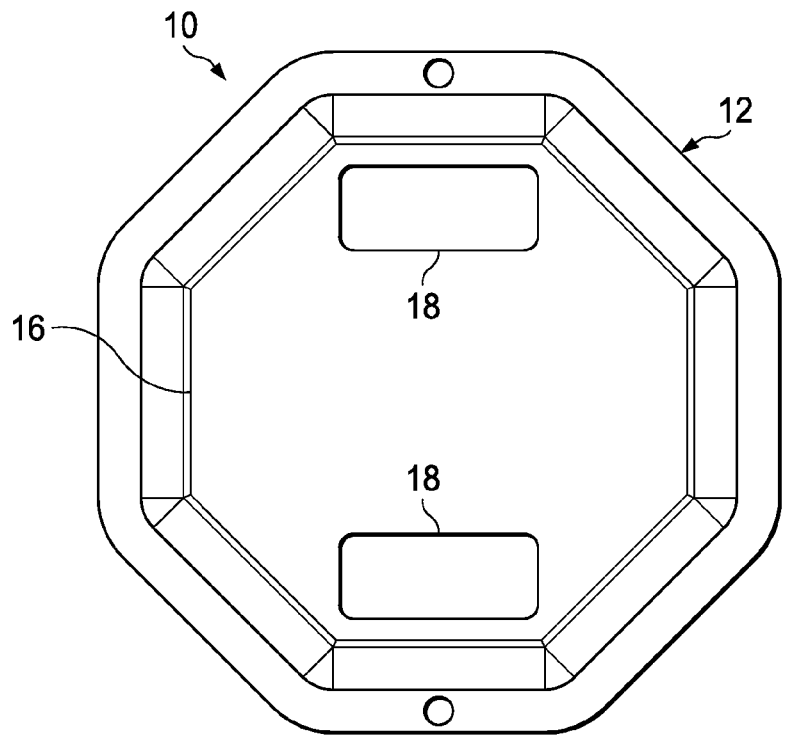
FIGS. 1A and 1B are diagrams illustrating respective front and rear views of an embodiment of an impact indicator according to the present disclosure.
Figure 1B:
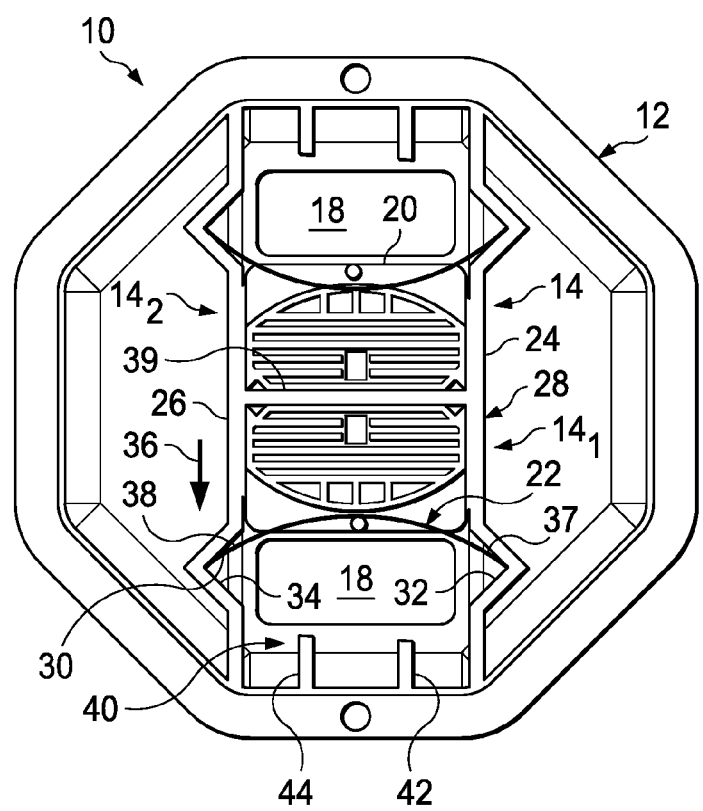

With reference now to the Figures and in particular with reference to FIGS. 1A and 1B, exemplary diagrams of an impact indicator 10 are provided in which illustrative embodiments of the present disclosure may be implemented. FIG. 1A is a diagram illustrating a front view of impact indicator 10, and FIG. 1B is a diagram illustrating a rear view of impact indicator 10. In FIGS. 1A and 1B, indicator 10 is a portable device configured to be affixed to or disposed within a transport container containing an object of which impact and/or acceleration events associated therewith are to be monitored. Embodiments of impact indicator 10 monitor whether an object has been exposed to an impact or some level of an acceleration event during manufacturing, storage and/or transport of the object. In some embodiments, impact indicator 10 may be affixed to a transport container using, for example, adhesive materials, permanent or temporary fasteners, or a variety of different types of attachment devices. The transport container may include a container in which a monitored object is loosely placed or may comprise a container of the monitored object itself. It should be appreciated that FIGS. 1A and 1B are only exemplary and are not intended to assert or imply any limitation with regard to the environments in which different embodiments may be implemented.

In the embodiment illustrated in FIGS. 1A and 1B, impact indicator 10 comprises a housing 12 having one or more impact assemblies 14 disposed therein (e.g., depicted as assembly $14_1$ and $14_2$ in FIG. 1B). For example, as best illustrated in FIG. 1B, the illustrated embodiment includes two internal detection assemblies 14 for detecting and indicating impact or acceleration events in either of two different directions. However, it should be understood that impact indicator 10 may be configured having a greater or fewer quantity of detection assemblies 14 (e.g., a single assembly 14 for detecting/indicating an impact event corresponding to a single direction or three or more assemblies 14 for detecting/indicting an impact event in three or more directions).

In some embodiments, housing 12 is configured and/or constructed from a clear or semi-opaque material having a masking label 16 located on a front side thereof or affixed thereto (FIG. 1A). In some embodiments, masking label 16 is configured having one or more apertures or "windows" 18 for providing a visual indication of impact detection. For example, as will be described further below, in response to indicator 10 being subjected to or receiving some predetermined level of impact or acceleration event, detection assembly 14 causes a visual indication to be displayed within or through one or more of windows 18 to provide a visual indication that the monitored object has or may have been subjected to some level of impact. However, it should be understood that other methods may be used to provide a visual indication that detection assembly 14 has moved and/or been otherwise placed into an activated state indicating that indicator 10 has experienced a shock, impact or acceleration event. It should also be understood that housing 12 may be configured and/or manufactured from other materials (e.g., opaque materials having one or more windows 18 formed therein).

Referring to FIG. 1B, detection assemblies $14_1$ and $14_2$ are illustrated in a non-activated or initial pre-detection state (i.e., prior to being subjected to an acceleration event). As illustrated in FIG. 1B, detection assemblies $14_1$ and $14_2$ are located adjacent to respective windows 18 such that no visual indication of a detected impact is provided via windows 18. For ease of description and illustration, detection assembly $14_1$ is described below; however, it should be understood that assembly $14_2$ may be similarly configured. In the illustrated embodiment, detection assembly $14_1$ comprises a weight or mass member 20 and a spring member 22. Housing 12 comprises sidewalls 24 and 26 located on opposite sides of mass member 20. Sidewalls 24 and 26 form a translation path to enable movement of mass member 20 within housing 12 in response to housing 12 or indicator 10 being subjected to an acceleration event. For example, in FIG. 1B, mass member 20 is located in a non-activated position 28 within housing 12. In the illustrated embodiment, spring member 22 biases mass member 20 to the non-activated position 28 in the pre-detection state of indicator 10. For example, in the illustrated embodiment, spring member 22 comprises a leaf spring 30; however, it should be understood that other types of biasing elements may be used. In FIG. 1B, sidewalls 24 and 26 have formed therein recesses or seats 32 and 34 for holding each respective end 37 and 38 of leaf spring 30. Leaf spring 30 is formed having a length greater than a width of mass member 20 (e.g., as measured in a direction from sidewall 24 to sidewall 26). The ends 37 and 38 of leaf spring 30 are located in seats 32 and 34 such that leaf spring 30 is positioned in an orientation transverse to the movement path of mass member 20. For example, the translation path formed by sidewalls 24 and 26 enables movement of mass member 20 in a direction indicated by 36. Ends 37 and 38 of leaf spring 30 are located in respective seats 32 and 34 such that leaf spring 30 has a convex surface thereof in contact with a portion and/or surface of mass member 20 to bias mass member 20 to the non-activated position 28 (e.g., biasing mass member 20 toward and/or against a wall 39 within housing 12).

In the embodiment illustrated in FIG. 1B, housing 12 is formed having offset surface portions 40 corresponding to and/or near an activated position of assembly $14_1$ (e.g., when mass member 20 is located in a position and/or within an area corresponding to window 18). In the illustrated embodiment, offset surface portions 40 are formed by support posts 42 and 44 having different lengths (e.g., in the illustrated embodiment, support post 44 has a length greater than a length of support post 42). However, it should be understood that offset surface portions 40 may be otherwise formed (e.g., and angled planar surface). As will be described further below, offset surface portions 40 facilitate the rotation of mass member 20 when in the activated position to facilitate retention of mass member 20 in the activated position after acceleration event detection (i.e., to prevent or substantially prevent mass member 20 from returning to the non-activated position 28).

Figure 2A:
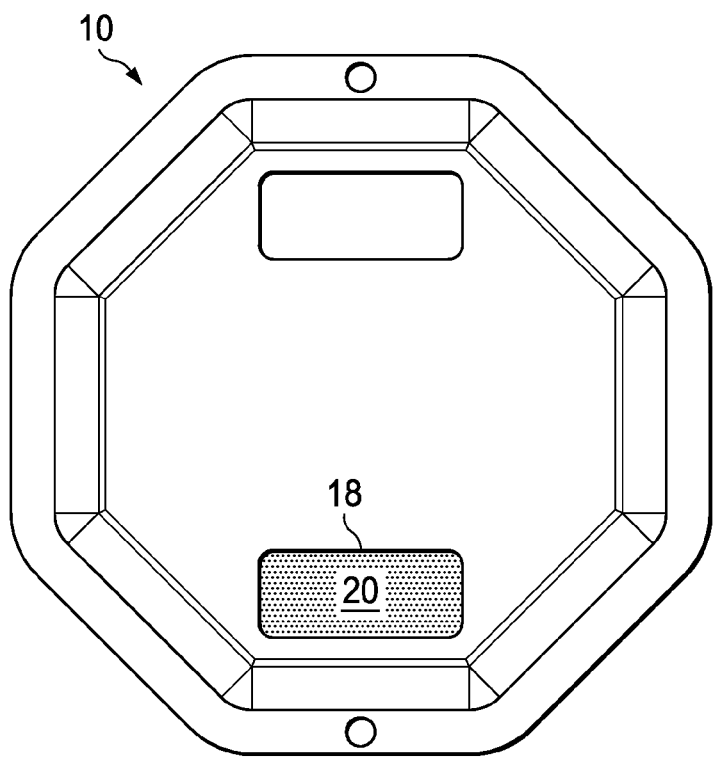
FIGS. 2A and 2B are diagrams illustrating respective front and rear views of the impact indicator of FIGS. 1A and 1B in an activated state according to the present disclosure.
Figure 2B:
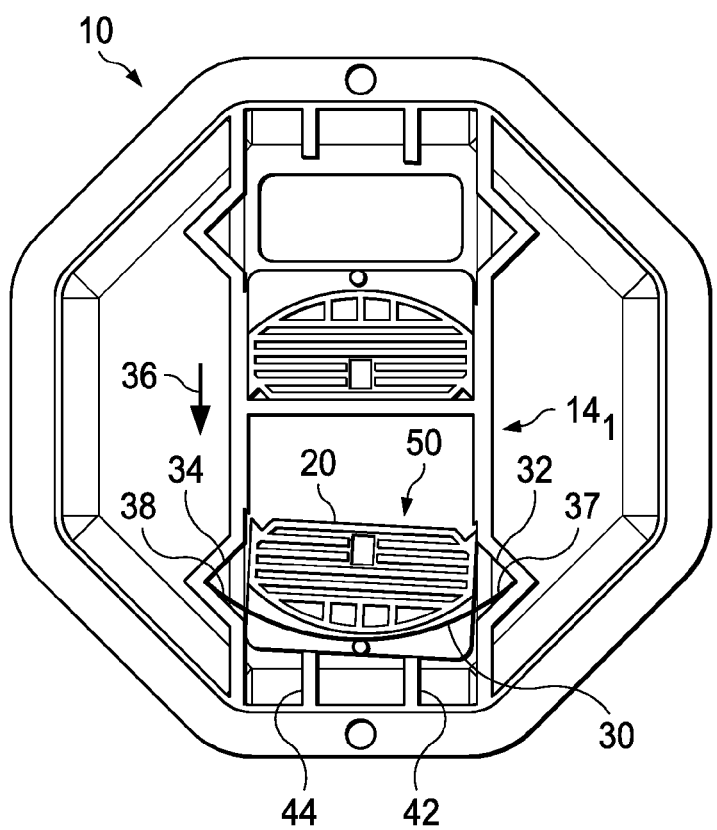

FIGS. 2A and 2B are diagrams illustrating a front and rear view, respectively, of indicator 10 of FIGS. 1A and 1B in an activated state. For example, as illustrated in FIG. 1B, mass member 20 has moved from the non-activated position 28 to an activated position 50 within housing 12. For example, in response to indicator 10 and/or housing 12 otherwise receiving an acceleration or impact event in a direction corresponding to direction 36 (i.e., in direction 36 or at an angle thereto having a directional vector component in direction 36) of a certain and/or predetermined level or magnitude, mass member 20 overcomes the bias of leaf spring 30, thereby causing leaf spring 30 to deform and/or otherwise invert and enabling mass member 20 to move in the direction 36 to the activated position 50. As best illustrated in FIG. 2A, when mass member 20 is in the activated position 50, mass member 20 is located within an area corresponding to at least a portion of window 18 such that mass member 20 located in activated position 50 provides a visual indication of activation of indicator 10 via window 18. In some embodiments, mass member 20 may comprise a color coding, alphanumeric indicia, or other type of indicia on a surface thereof that is visible through window 18 when mass member 20 is located in the activated position 50.

Figure 3:
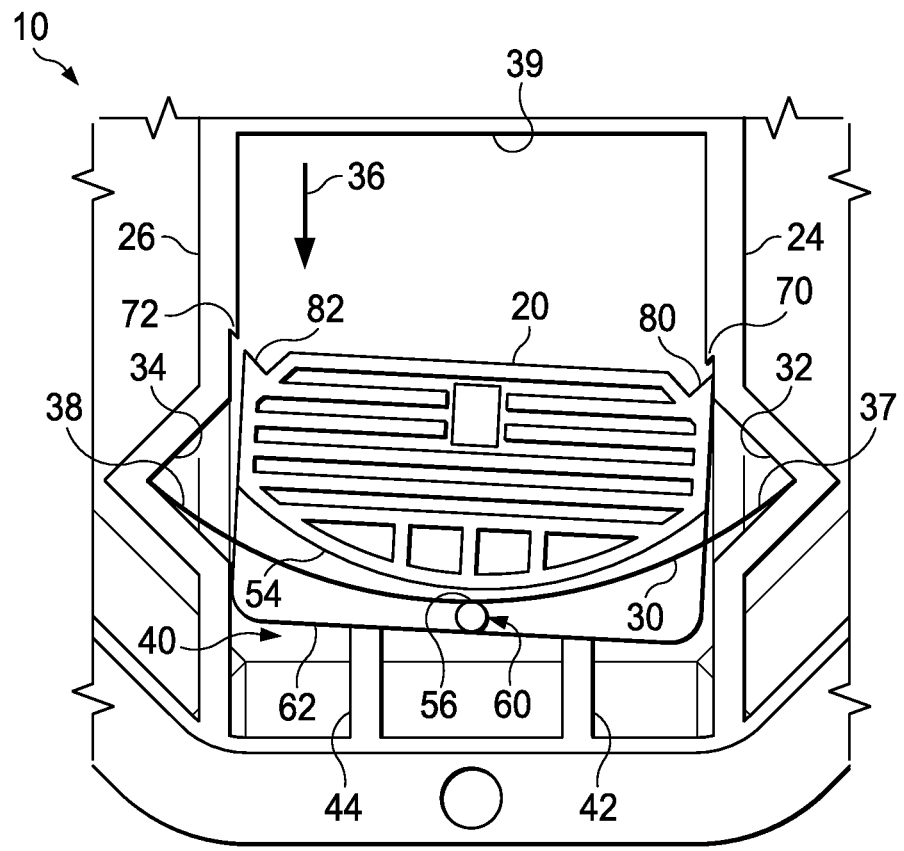
FIG. 3 is a diagram illustrating an enlarged view of a portion of the impact indicator illustrated in FIG. 2B in accordance with the present disclosure.
Figure 4:
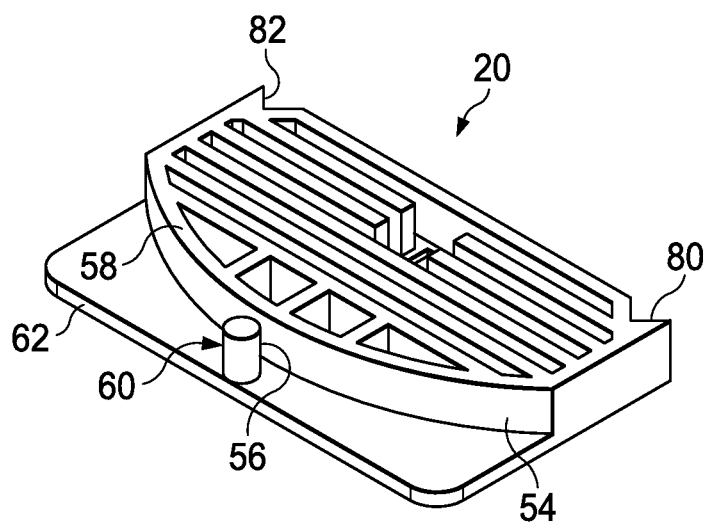
FIG. 4 is a diagram illustrating an embodiment of a mass member of the impact indicator illustrated in FIGS. 1A and 1B according to the present disclosure.

FIG. 3 is a diagram illustrating an enlarged view of a portion of FIG. 2B, and FIG. 4 is a diagram illustrating a perspective view of an embodiment of mass member 20. Referring to FIGS. 2B, 3 and 4, in the activated position 50 (e.g., after leaf spring 30 inverts from the non-activated position as illustrated in FIG. 1B), leaf spring 30 biases mass member 20 in the direction 36 and causes mass member 20 to rotate and/or tilt relative to housing 12. For example, in the illustrated embodiment, leaf spring 30 is disposed between opposing surfaces 54 and 56 of mass member 20 such that, in the non-activated position 28, leaf spring 30 bears against surface 54 of a wall 58 of mass member 20, and in the activated position 50, leaf spring 30 bears against surface 56. In the illustrated embodiment, surface 56 is located on a pivot pin 60 of mass member 20; however, it should be understood that the configuration of mass member 20 may vary to provide opposing surfaces 54 and 56 for different leaf spring 30 biasing directions. In the illustrated embodiment, pivot pin 60 of mass member 20 comprises an eccentric pivot pin 60 such that a contact position of pivot pin 60 by leaf spring 30 is offset from an inertial center of mass member 20, thereby causing rotation of mass member 20 when in the activated position 50. For example, in the embodiment illustrated in FIG. 3, pivot pin 30 is located offset from an inertial center of mass member 20 toward support post 42 (e.g., where support posts 42 and 44 are located at generally a same distance from the inertial center of mass member 20 in a width direction of mass member 20) such that leaf spring 30 bears against eccentric pivot pin 60 to cause rotation and/or turning of mass member 20 in the activated position 50. It should be understood that mass member 20 may be otherwise configured having an eccentric or offset from inertial center contact surface/point to facilitate rotation thereof by leaf spring 30.

In the embodiment illustrated in FIGS. 2B, 3 and 4, leaf spring 30 also biases mass member 20 toward offset surface portions 40 (e.g., support posts 42 and 44). For example, after leaf spring 30 inverts from the non-activated position as illustrated in FIG. 1B to the activated position illustrated in FIGS. 2B and 3, leaf spring 30 bears against pivot pin 60 and causes a side or surface 62 of mass member 20 to be biased against support posts 42 and 44. Support posts 42 and 44, by having offset contact surfaces relative to mass member 20, facilitate the rotation of mass member 20 in the activated position 50.

As best illustrated in FIG. 3, sidewalls 24 and 26 each have formed thereon a respective latch element 70 and 72 for engaging a corresponding latch element 80 and 82 formed on mass member 20 to prevent or substantially prevent mass member 20 to returning to the non-activated position 28. For example, in the illustrated embodiment, rotation of mass member 20 in the activated position 50 facilitates retention of mass member 20 in the activated position 50 once therein by causing latch element 80 to become positioned and/or otherwise aligned for engagement with latch element 70 in sidewall 24. If indicator 10 and/or housing 12 is subjected to another acceleration event in a direction opposite direction 36 (e.g., an unauthorized attempt to reset indicator 10), movement of mass member 20 in a direction opposite direction 36 causes latch element 80 to engage latch element 70, thereby preventing movement of mass member upwardly toward non-activated position 28.

In the illustrated embodiment, latch element 72 is located offset from latch element 70 to further prevent or substantially prevent mass member 20 from returning to the non-activated position 28 once indicator 10 has been activated. For example, with respect to a vertical location of latch elements 70 and 72 (e.g., as measured along a direction such as a direction aligned with direction 36), latch element 72 is located at a greater distance from, for example, seat 34, than a distance from latch 70 to seat 32 (or, latch 72 is located closer in distance to wall 39 than latch 70). In operation, if indicator 10 receives an acceleration event in a direction opposite direction 36 (or at a slight angle opposite to direction 36) such that the rotated position of mass member 20 is overcome, latch 82 of mass member 20 becomes positioned and/or otherwise aligned for engagement with latch element 72 in sidewall 26. Thus, if an acceleration event causes reverse rotation of mass member 20 and directional movement in a direction opposite direction 36 such that latch member 80 avoids engagement with latch element 70, latch element 82 engages latch element 72 to prevent or substantially prevent mass member 20 from returning to the non-activated position 28.

In some embodiments, spring member 22 is selected and/or otherwise configured to bias and/or otherwise retain mass member 20 in the non-activated position 28 until and/or unless a predetermined level or magnitude of impact/acceleration is experienced by indicator 10. For example, the tension force of spring member 22 retains mass member 20 in the non-activated position and, in response to indicator 10 receiving an acceleration event in a direction opposite the tension force of spring member 22 of a magnitude exceeding the tension force applied by spring member 22 to mass member 20, spring member 22 inverts and/or otherwise reverses it orientation enabling mass member 20 to move to the activated position 50. Impact indicator 10 may be configured for various levels of impact or acceleration activation by setting a particular weight of mass member 20, selecting/configuring a particular thickness and/or material of spring member 22, etc. For example, in some embodiments, spring member 22 may be configured from a polymer material (e.g., such as a Duralar® material) that may maintain a substantially constant spring tension force over a desired temperature spectrum, thereby alleviating an inadvertent activation of indicator 10 that may otherwise result from a temperature change.

Thus, embodiments of the present disclosure enable impact and/or acceleration event detection while preventing or substantially preventing a re-setting of the state of the impact indicator 10 once a predetermined level or magnitude of impact has occurred. For example, in some embodiments, the mass member 20 of indicator 10 is configured to rotate in response to moving from the non-activated position 28 to the activated position 50 to facilitate retention of mass member 20 in the activated position 50 once indicator 10 has been activated. Further, embodiments of the present disclosure further enable retention of the mass member 20 in the activated position once indicator 10 has been activated by using a plurality of offset latches that are configured to engage the mass member 20 if indicator 10 receives an acceleration event that may be performed in an attempt to re-set indicator 10 to the non-activated state.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. An impact indicator, comprising:
   a housing;
   a mass member located within the housing, the housing configured to enable movement of the mass member from a first position to a second position within the housing in response to receipt of an acceleration event by the housing; and
   a spring member disposed within the housing and configured to bias the mass member to the first position, and wherein in response to receipt by the housing of the acceleration event, the mass member is configured to overcome the bias and move from the first position to the second position; and
   wherein the mass member comprises an eccentric pivot member to cause rotation of the mass member within the housing in the second position to enable retention of the mass member in the second position.

2. The impact indicator of claim 1, wherein the housing comprises first and second internal support posts, the first support post having a length greater than a length of the second support post to facilitate rotation of the mass member in the second position.

3. The impact indicator of claim 1, wherein the spring member comprises a leaf spring having a length greater than a width of the mass member and disposed transversely to a direction of movement of the mass member.

4. The impact indicator of claim 3, wherein the leaf spring extends between an eccentric pivot member of the mass member and a wall of the mass member.

5. The impact indicator of claim 1, wherein the housing comprises a window to enable a visual indication of the mass member located in the second position.

6. The impact indicator of claim 1, wherein the housing comprises a plurality of sidewalls forming a translation path for movement of the mass member from the first position to the second position, and wherein at least one of the sidewalls includes a latch element configured to engage a corresponding latch element formed on the mass member to retain the mass member in the second position in response to receipt by the housing of another acceleration event in an opposite direction.

7. The impact indicator of claim 1, wherein the housing comprises a first latch element located proximate to a first side of the mass member and a second latch element located proximate to a second side of the mass member opposite the first side and offset from the first latch element, the first and second latch elements configured to engage corresponding latch elements located on the mass member to retain the mass member in the second position in response to the housing receiving another acceleration movement in an opposite direction.

8. An impact indicator, comprising:
   a housing;
   a mass member located within the housing, the housing configured to enable movement of the mass member from a first position to a second position within the housing in response to receipt by the housing of a first acceleration event;
   a spring member disposed within the housing and configured to bias the mass member to the first position, and wherein in response to receipt by the housing of the first acceleration event, the mass member overcomes the bias and moves from the first position to the second position; and a first latch element located proximate to a first side of the mass member and a second latch element located proximate to a second side of the mass member opposite the first side and offset from the first latch element, at least one of the first and second latch elements configured to engage a corresponding latch element located on the mass member to retain the mass member in the second position in response to the housing receiving a second acceleration event in a direction opposite the first acceleration event.

9. The impact indicator of claim 8, wherein the housing comprises first and second internal support posts, the first support post having a length greater than a length of the second support post to cause rotation of the mass member within the housing in the second position.

10. The impact indicator of claim 8, wherein the spring member comprises a leaf spring having a length greater than a width of the mass member and disposed transversely to a direction of movement of the mass member.

11. The impact indicator of claim 8, wherein the housing comprises a window to enable a visual indication of the mass member located in the second position.

12. The impact indicator of claim 8, wherein the housing comprises first and second sidewalls located on opposite sides of the mass member forming a translation path for the mass member to move from the first position to the second position, and wherein the first and second latch elements are disposed on the respective first and second sidewalls.

13. An impact indicator, comprising:
   a housing;
   a mass member located within the housing, the housing having a plurality of sidewalls forming a translation path to enable movement of the mass member from a first position to a second position within the housing in response to receipt by the housing of an acceleration event; and
   a spring member disposed within the housing and configured to bias the mass member to the first position, and wherein in response to receipt by the housing of the acceleration event, the mass member moves from the first position to the second position and the spring member bears on the mass member to cause rotation of the mass member in the second position to facilitate retention of the mass member in the second position; and
   wherein at least one of the sidewalls is configured to engage a portion of the mass member to retain the mass member in the second position in response to receipt by the housing of another acceleration event in an opposite direction.

14. The impact indicator of claim 13, wherein the spring member comprises a leaf spring disposed transversely to a direction of movement of the mass member, the leaf spring bearing on the mass member in the second position to cause rotation of the mass member in the second position.

15. The impact indicator of claim 14, wherein the leaf spring extends between adjacent facing portions of the mass member.

16. The impact indicator of claim 14, wherein the leaf spring extends between an eccentric pivot member of the mass member and a wall of the mass member.

17. The impact indicator of claim 13, wherein the housing comprises a window to enable a visual indication of the mass member located in the second position.

18. The impact indicator of claim 13, wherein the spring member biases the mass member in the second position against a portion of the housing to cause rotation of the mass member in the second position.

19. The impact indicator of claim 18, wherein the portion of the housing comprises offset surface portions.

\* \* \* \* \*